United States Patent [19]
Evers

[11] Patent Number: 5,171,536
[45] Date of Patent: Dec. 15, 1992

[54] COLORIMETRIC TESTING AND MEASURING DEVICE FOR GASES

[75] Inventor: Wolfgang Evers, Lübeck, Fed. Rep. of Germany

[73] Assignee: Drägerwerk Aktiengesellschaft, Lübeck, Fed. Rep. of Germany

[21] Appl. No.: 804,063

[22] Filed: Dec. 9, 199117153653100242286

[51] Int. Cl.$^5$ .............................................. G01N 30/00
[52] U.S. Cl. .................................... 422/88; 422/86; 422/87; 436/104; 436/167; 436/169
[58] Field of Search ........................... 422/86, 87, 88; 436/104, 167, 169; 73/23.2

[56] References Cited

U.S. PATENT DOCUMENTS

| | | | |
|---|---|---|---|
| 1,644,014 | 10/1927 | Gordon et al. | 422/86 |
| 4,731,333 | 3/1988 | Kitahara et al. | 436/167 |
| 4,737,166 | 4/1988 | Matson | 55/16 |
| 4,883,505 | 11/1989 | Lucero | 73/863.11 |

FOREIGN PATENT DOCUMENTS 2853430  6/1979  Fed. Rep. of Germany ........ 422/86

Primary Examiner—Robert J. Warden
Assistant Examiner—Laura E. Collins
Attorney, Agent, or Firm—Walter Ottesen

[57] ABSTRACT

The invention is directed to a testing and measuring device for colorimetrically detecting gases on a carrier which is impregnated with a solution of a moisture store and a detecting indicator. The testing and measuring device is improved in that the moisture on the indicator carrier needed for the detecting reaction is maintained over a longer time span during storage in the unused condition as well as during measurement under the action of the gaseous substance to be detected. For this purpose, the impregnating solution is composed of the detecting indicator and a mixture of sulfolane and diethylphthalate as a moisture store. For measuring hydride gases, the indicator comprises a palladium tetramine chloride. The impregnating solution is applied to a paper carrier or to a granular silica gel carrier.

4 Claims, 1 Drawing Sheet

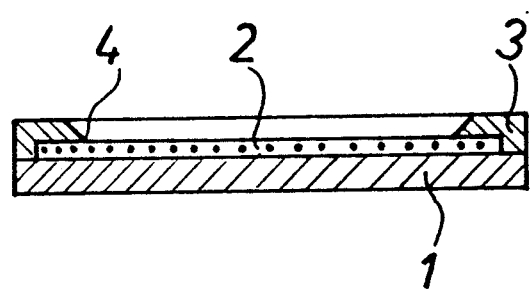

5,171,536

COLORIMETRIC TESTING AND MEASURING DEVICE FOR GASES

RELATED APPLICATION

This is a continuation-in-part of application Ser. No. 584,140, filed on Sep. 19, 1990, now U.S. Pat. No. 5,075,081 and entitled "Colorimetric Testing and Measuring Device for Hydride Gas".

FIELD OF THE INVENTION

The invention relates to a testing and measuring device for colorimetrically detecting hydride gases on a carrier which is impregnated with a solution of glycol and a salt as an indicator. The invention further relates to a testing and measuring device for colorimetrically detecting gaseous substances wherein the device includes the carrier for a detecting indicator which is impregnated on a carrier together with an additive serving as a moisture store.

BACKGROUND OF THE INVENTION

A testing and measuring device of the kind first mentioned above is described in U.S. Pat. No. 4,420,567.

The reliable detection of hydride gases such as arsine or phosphine as highly toxic constituents in chemical processes, such as in the semiconductor industry, is becoming ever more necessary and requires an apparatus which can be manipulated in a simple manner and which provides a reliable indication. The known indicator operates on the principle of coloration change of an indicator substance in the presence of the hydride gas to be detected. An indicator is impregnated, for example, on a paper tape and provided with impregnation additives. The degree of coloration is measured either by a color comparison or by a linear coloration of the indicator tape. Spectro-photometric evaluation possibilities are also available.

The constituents of the known indicator include silver nitrate together with an acid and a glycol impregnated on a carrier substrate. Since the silver nitrate alone is light sensitive and a long-term stability of the indicator is assured only in short time spans, an acid additive is required to improve the long-term stability. However, this indicator provided with an acid additive also shows an unchanged detection characteristic only over a time span of approximately six months. This stabilization duration is too short to prevent a light-induced coloration of the indicator over a longer time span. However, this is desirable since the storage capability of the unused indicator is required over a significantly longer time span. Faulty measurements because of the effect of light during the detection of the hydride gas have to be avoided.

A further indicator for hydride gases is described in European Patent Publication EP-Al 206 815. A copper salt is used as a detecting reagent and especially copper carbonate is utilized. This detection system is however not sufficiently recognizable with respect to hydride gases in its coloration because the initial blue color of the indicator in the presence of the hydride gas turns black; however, this color change cannot be detected with the naked eye especially for small concentrations to be detected. Accordingly, this known indicator is only suitable where high concentrations are to be detected.

SUMMARY OF THE INVENTION

It is an object of the invention to provide an indicator of the kind described above which is so improved that its long-term stability is improved even under the action of light. It is another object of the invention that the coloration of the indicator is clearly recognizable in the presence of hydride gases and especially for the smallest quantities to be detected.

According to a feature of the invention, only palladium (II) chloride is provided as a salt in addition to the glycol.

The advantage of the invention is seen in that the indicator retains its original yellow/orange basic color even under intensive light radiation without a further additive such as an acid so that its long term stability for a period of time greater than two years is assured. A turnover of the yellow/orange coloration into a grey coloration in the presence of hydride gases is easily determined by the observer. Also, storage under increased temperatures does not lead to undesired color changes. In this way, a simple indicator solution comprising few components is obtained for detecting hydride gases. The indicator solution is stable for a long period of time and can be used for example, in indicator tapes or colorimetric indicator tubes with impregnations which are easily recognizable with respect to their color change.

The object of the invention can also be realized in that in addition to glycol, only the salt palladium tetramine chloride is present in solution. Such a device affords not only the advantage of the indicators provided with palladium (II) chloride; but instead is usable especially for detecting the smallest quantity of hydride gases in the order of magnitude of 0.01 ppm. An indicator paper impregnated with this solution remains colorless even with intensive sunlight radiation. The contrast intense color changeover from white to grey in the presence of hydride gases makes even the smallest quantity to be detected clearly recognizable.

To further increase the sensitivity, it is advantageous to use tetraethylene glycol as a glycol substance.

To produce an impregnating solution suitable for the invention, the following:

0.5 grams palladium (II) chloride and
10 mL tetraethylene glycol are filled with methanol up to 100 mL. With the solution obtained in this manner, an indicator paper with or without silica gel is impregnated as the carrier substrate and is subjected to the hydride gas as a badge. The depth of coloration of yellow/orange into grey is a measure for the presence of the pollutant quantity. Likewise, a granular silica gel charge for a colorimetric testing tube can be impregnated with the solution and can be used to detect hydride gases. The length of the coloration zone of yellow/orange into grey is a measure of the concentration of the pollutant.

A further impregnating solution suitable for the invention comprises:

0.5 grams palladium (II) chloride dissolved in 5 mL ammonia for forming palladium tetramine chloride and
10 mL tetra-ethylene glycol filled with methanol up to 100 mL. An indicator impregnated with this solution has a white coloration which changes into grey in the presence of hydride gases.

With one of the solutions obtained in the manner described above, the indicator carrier such as an indicator paper or a granular silica gel charge is impregnated and subjected to the hydride gas.

The testing and measuring device described above operates to reliably detect, for example, hydride gases such as arsine or phosphine as highly toxic constituents in chemical processes such as in the semiconductor industry. A reliably detecting device which is easy to manipulate is needed for this purpose. For many indicating materials such as palladium salt utilized in the known dosimeter for detecting hydride gases, it is necessary that the indicator is provided with a certain degree of moisture during storage in the unused condition as well as for longer continuous measurement durations. This is necessary so that, on the one hand, an exsiccation is avoided during storage while, on the other hand, the necessary moisture is available which is adequate for the coloration reaction during the measuring operation.

Glycol and especially ethylene glycol are used as the moisture stores in the device described above for detecting hydride gases. However, since measuring time spans for a continuous monitoring of air are required which are becoming ever longer, glycol as a moisture store is not adequate for all situations. Long-term measurements typically require a time span of 8, 12 and even 24 hours. Accordingly, there is generally a requirement imposed on a moisture store in the impregnated solution of a colorimetric testing and measuring device which must take account of these extended measuring time spans.

In view of the above, it is another object of the invention to provide a testing and measuring device of the kind described above which is improved so that the moisture on the indicator carrier which is required for the detecting reaction is maintained over a longer time span during storage in the unused condition as well as when subjected to the gaseous substance to be detected.

According to a feature of the testing and measuring device of the invention, a moisture store is provided in the form of a mixture of sulfolane and diethylphthalate.

The advantage of this embodiment of the invention is essentially seen in that a significantly longer storage action is obtained for the moisture required for the detection whereby an exsiccation of the indicator over a longer continuous measuring time is prevented even when the indicator is exposed to a relatively dry gas to be measured. Such a humidity store is not only suitable for indicators for detecting hydride gases; instead, it can be used anywhere where the detecting indicator must have a certain degree of moisture for forming a color reaction with the gaseous substance to be detected.

Sulfolane is the conventional name for tetrahydrothiophene (1.1) dioxide. Diethylphthalate is another name for the substance phthalic acid diethylester.

An especially suitable mixture ratio of sulfolane and diethylphthalate is 10 parts sulfolane to one part diethylphthalate. Such a mixture has a melting point of 0° C. whereby the use of such a detector indicator having the impregnating solution is made possible in a temperature range of 2° C. to 40° C. The vapor pressure is less because of the lower melting point and because of this vapor pressure, a detecting indicator having an impregnating solution of this kind does not dry out even for a continuous measurement longer than eight hours.

For measuring hydride gases, it is advantageous to process the moisture store with palladium (II) chloride as an indicator to an impregnating solution. This impregnating solution affords the advantage that it is colorless over the above-mentioned longer time span and leads to a coloration which becomes clearly visible under the action of hydride gases.

Palladium tetramine chloride is likewise suitable as an indicator for measuring hydride gases. Both impregnating solutions for the detection of hydride gases have an excellent storage capability because of the long-term storage action of the sulfolane/diethylphthalate mixture and have an excellent detection sensitivity since the indicator, which is colorless when not subjected to the gas to be detected, leads to a clear coloration in the presence of a hydride gas.

For detecting, for example, phosphorus hydride, the suitable impregnating solution is produced as follows: 5 grams of pulverized palladium (II) chloride is placed in a measuring flask and is dissolved in 50 ml ammonia at approximately 100° C. After the ammonium surplus is removed and the solution has cooled down to room temperature, 100 ml water and 100 ml methanol is added. Thereafter, approximately 250 grams of a sulfolane/diethylphthalate mixture is added and filled with methanol as required. The impregnating solution produced in this manner is impregnated on the indicator carrier. The carrier can be a paper badge or a porous, granular silica gel carrier. The impregnated paper badge is, for example, clamped into a housing and utilized as a dosimeter in which the badge surface is exposed to the gas to be detected and the coloration resulting therefrom is applied as a measure for the quantity of the substance to be detected. The granular silica gel carrier is in turn filled, for example, into a testing tube and provides a colorimetric determination of gaseous toxic substances.

The example provided above describes a complete detector indicator as being a mixture in solution of palladium tetramine chloride, sulfolane and diethylphthalate with the palladium tetramine chloride being obtained from palladium (II) chloride to which ammonia has been added. In contrast, if palladium (II) chloride is to be used as a coloration indicator, then the preparation is undertaken in a similar manner but without mixing palladium (II) chloride with ammonia.

BRIEF DESCRIPTION OF THE DRAWING

The single figure of the drawing shows an embodiment of the testing and measuring device for gases in the form of a dosimeter.

DESCRIPTION OF THE PREFERRED EMBODIMENTS OF THE INVENTION

The testing badge shown in the drawing includes a disc-shaped badge carrier 1 of circular configuration on which a disc-shaped impregnated indicator paper 2 is positioned and which is held on the badge carrier 1 with a clamping edge 3. The ring-shaped clamping edge 3 defines a badge opening 4 through which the gas to be detected has access to the indicator paper 2. The gas there reacts with the indicator solution impregnated in the paper to form a color change the depth of which is a measure for the quantity collected during the period of exposure and is determined by comparison with a color standard. The impregnation can be a solution of palladium tetramine chloride and a sulfolane/phthalic acid diethylester mixture in the ratio of 10:1.

It is understood that the foregoing description is that of the preferred embodiments of the invention and that various changes and modifications may be made thereto without departing from the spirit and scope of the invention as defined in the appended claims.

What is claimed is:

1. A testing and measuring device for colorimetrically detecting gaseous substances, the device comprising:
a carrier on which gaseous substances are detected, said carrier being impregnated with a detecting indicator and a moisture store, said moisture store being a mixture of sulfolane and diethylphthalate.

2. The device of claim 1, wherein said mixture of sulfolane and diethylphthalate is 10:1 based on the percent by weight of the sulfolane to diethylphthalate.

3. The device of claim 1, wherein a substance to be detected is a hydride gas and said detecting indicator is a palladium (II) chloride.

4. The device of claim 1, wherein a substance to be detected is a hydride gas and said detecting indicator is a palladium tetramine chloride.

* * * * *

UNITED STATES PATENT AND TRADEMARK OFFICE
CERTIFICATE OF CORRECTION

PATENT NO. : 5,171,536

DATED : December 15, 1992

INVENTOR(S) : Wolfgang Evers

It is certified that error appears in the above-identified patent and that said Letters Patent is hereby corrected as shown below:

On the title page: Item [22] delete
"Dec. 9, 199117153653100242286" and substitute
-- Dec. 9, 1991 -- therefor.

between item [22] and item [51]: please insert:
-- [30]        Foreign Application Priority Data
    Sep. 22, 1989 [DE]    Fed. Rep. of Germany .... 3931563
    Jun. 29, 1990 [DE]    Fed. Rep. of Germany .... 4020753
    Jun. 29, 1991 [DE]    Fed. Rep. of Germany .... 4121633 --.

Item [56] under "References Cited": delete
"4,737,166  4/1988  Matson ..................... 55/16"
and substitute therefor
-- 4,737,166  4/1988  Matson et al ............. 55/16 --.

Signed and Sealed this

Seventh Day of December, 1993

Attest:

Attesting Officer

BRUCE LEHMAN

Commissioner of Patents and Trademarks